United States Patent [19]

Gigante

[11] Patent Number: 5,445,626
[45] Date of Patent: Aug. 29, 1995

[54] VALVE OPERATED CATHETER FOR URINARY INCONTINENCE AND RETENTION

[76] Inventor: Luigi Gigante, Via Riociarelli, 157, I-44100 Aguscello, Italy

[21] Appl. No.: 244,541
[22] PCT Filed: May 15, 1992
[86] PCT No.: PCT/IT92/00051
§ 371 Date: Jun. 3, 1994
§ 102(e) Date: Jun. 3, 1994
[87] PCT Pub. No.: WO93/10845
PCT Pub. Date: Jun. 10, 1993

[30] Foreign Application Priority Data

Dec. 5, 1991 [IT] Italy .................. BO901A459

[51] Int. Cl.⁶ .................................................. A61F 5/44
[52] U.S. Cl. .................................. 604/349; 600/29; 600/30
[58] Field of Search .................. 604/349–353, 604/174, 177; 600/29, 30

[56] References Cited

U.S. PATENT DOCUMENTS

| | | | |
|---|---|---|---|
| 1,661,494 | 3/1928 | Nielsen | 604/174 |
| 2,764,975 | 10/1956 | Greenberg | 604/174 |
| 4,923,938 | 6/1990 | Goldberg et al. | 604/96 |
| 4,946,449 | 8/1990 | Davis, Jr. | 604/256 |
| 5,087,252 | 2/1992 | Denard | 604/349 |

FOREIGN PATENT DOCUMENTS

WO90/04431 5/1990 WIPO.

*Primary Examiner*—Jerome L. Kruter
*Attorney, Agent, or Firm*—McAulay Fisher Nissen Goldberg & Kiel

[57] ABSTRACT

A valve operated catheter for urinary incontinence and retention comprises a flexible duct (2) designed to be inserted in the patient's urethra, the catheter provided with a spiral shaped end portion (12), having a plurality of holes (16) for the passage of urine. The duct 2 is provided, at its other end, with a seat (21) in which there is housed a valve (20) made of elastic material, the valve being usually closed because of the elastic action. The valve (20) may be operated by the patient through light compressive action on two winglets (25) which are fixed to the end of the duct near to the valve, the winglets positioned symmetrically to the longitudinal axis of the same valve, outside the top of glans, so as to cause the opening of the passage (22) through elastic deformation of the valve (20).

8 Claims, 1 Drawing Sheet

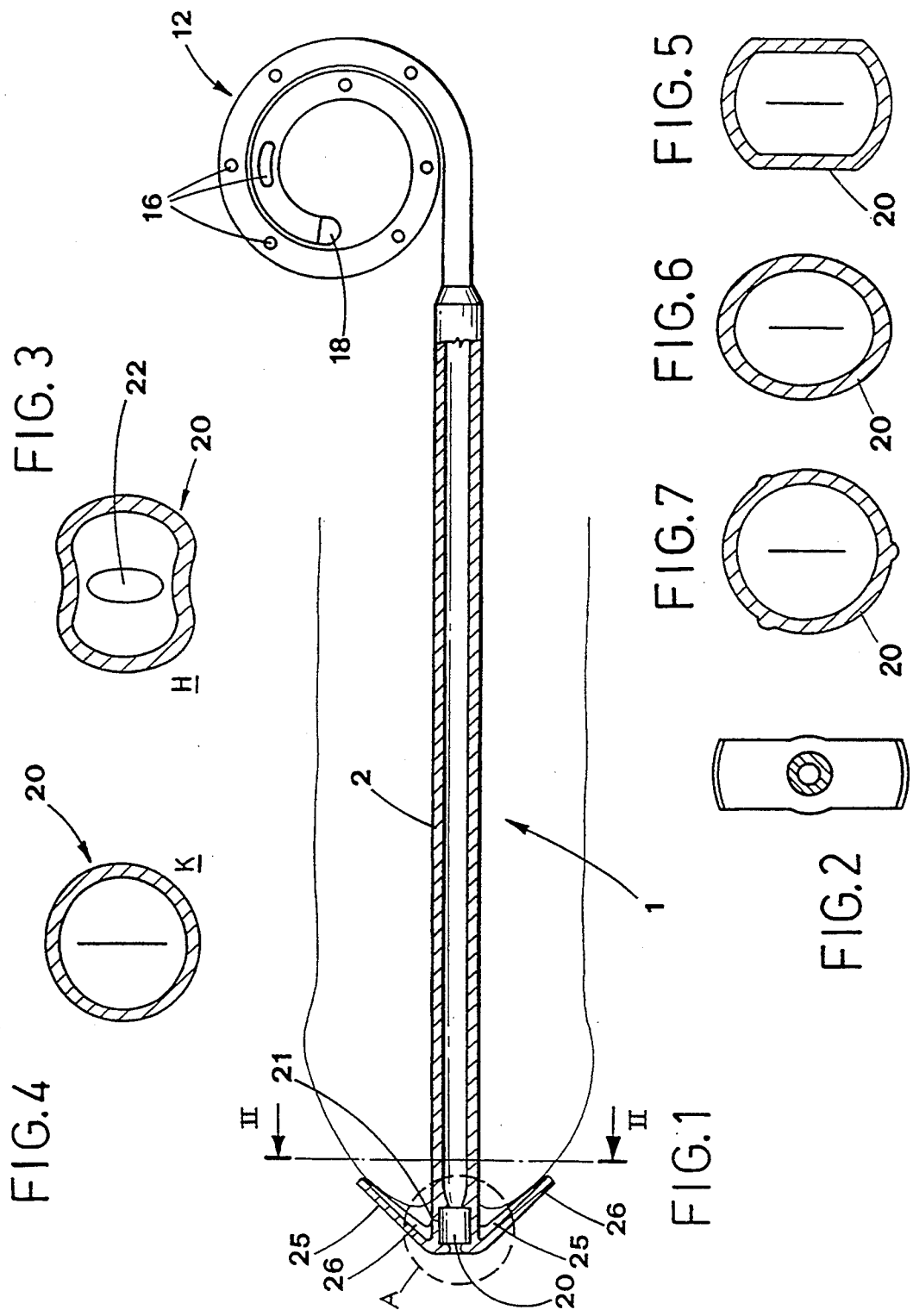

VALVE OPERATED CATHETER FOR URINARY INCONTINENCE AND RETENTION

TECHNICAL FIELD

The invention relates to the production of vesical catheters.

Such catheters are commonly used by patients to eliminate, or at least relieve, problems caused by urinary incontinence and retention.

BACKGROUND ART

Valve operated vesical catheters made of plastic material or, more generally, of synthetic resin are known.

These catheters generally consist of flexible ducts produced in various standardized lengths.

A catheter having a certain length must be chosen in accordance with the actual patients' need.

One catheter that is presently used is provided with a valve of elastic material, housed inside the duct close to the outer opening.

The valve can be operated by the patient through a slight pressure exerted from outside on a section of the penis which corresponds with the point of location of the valve.

This point can be located by the patient through a series of protuberances specially formed on the outside surface of the duct, near to the valve.

The distal end of the duct is positioned inside the bladder and has a spiral shape.

There are numerous holes provided along the terminal section of the catheter near the distal end, for urine to enter the catheter.

The principal drawback with the use of the above described catheters, results from the fact that it is difficult for the patient to locate the valve by touch, particularly as poor touch sensibility occurs in many patients who use these catheters.

A further inconvenience that has been found when such a catheter is used, results from the fact that the patient must apply pressure on the penis to operate the valve.

In the long run this, pressure that often is not light, could provoke more or less serious local traumas, with damage to the penis.

DISCLOSURE OF THE INVENTION

The main object of the present invention is to provide a catheter having a system that allows the patient to operate the valve directly and not through the penis, with a simple and safe action.

A further object of the present invention is to provide an easily adaptable catheter that can be used by any patient without causing traumas to any of the urinary system organs.

The above indicated objects are achieved by means of a valve operated catheter for urinary incontinence and retention comprising a flexible duct designed to be inserted into the patient's urethra and having a spiral shaped distal portion 12, that is designed to be housed inside the bladder.

A terminal section of the catheter, near to its distal end, is provided with a plurality of holes for the outflow of urine from the bladder to the inside of the duct.

A seat is made at an end of the catheter that remains outside the penis, the end housing a valve which is elastically deformable, the valve having a slit which is normally elastically closed.

The valve can be operated by the patient by pressing on two winglets fixed at the end of the duct, the winglets resting against the top of the glans.

In this way, deformation of the part of the duct correspondent which corresponds to the seat causes the elastic deformation of the valve until the slit opens.

The main advantage of the present invention is that it provides a catheter with a system for operating the valve that is immediately locatable by the patient, therefore, it is simple and safe to use.

The system that is the subject of this invention allows the patient to operate the valve of the catheter without pressing on the penis.

A further advantage of the present invention is that it provides a catheter of a simple construction and that it can be used by any patient without provoking traumas of any urinary system organs.

It is to be stressed that the patient does not have to press directly on the penis in any way.

The winglets remains located outside of the penis so that they can be quickly and easily located, even if the patient has poor touch sensibility.

Nevertheless the construction of the catheter is rather compact and the duct does not extend from the glans.

BRIEF DESCRIPTION OF THE DRAWINGS

The features of the invention will be pointed out in the following description with the help of the accompanying drawings, in which:

FIG. 1 is a sectional view of the catheter that is the subject of the present invention;

FIG. 2 is a cross sectional view taken along line II—II of FIG. 1;

FIG. 3 is a sectional view of the valve of FIG. 1 when it is open;

FIG. 4 is a sectional view of the valve of FIG. 1 when it is closed;

FIGS. 5, 6 and 7 show the valve made with a polygonal section, an oval section and with blocking protrusions, respectively.

MODES OF CARRYING OUT THE INVENTION

With reference to the figures, a catheter 1 includes a duct 2 made of flexible material, for instance a silicone material.

The duct 2 is particularly adapted to be inserted in the urethra by means of a rigid body, generally called a mandrel, designed to be removed after the duct is in place.

The distal portion 12 of the duct, near to the distal end of the duct is designed to be positioned inside the bladder. This portion has a shape of a spiral and is elastically deformable.

The axis of the spiral is perpendicular to the duct.

The distal portion 12 has a plurality of holes 16, the last of which has a form of a slot, such that urine in the bladder may freely flow into the catheter.

As illustrated in FIG. 1, at the distal end of the catheter there is a capsule 18 holding a substance having a disinfecting and antibacterial action.

The spiral shaped distal portion 12, may be unrolled in an amount sufficient to achieve the length necessary for the other end to reach outside of the body.

At the end of the duct 2 situated outside the body there is a seat 21, inside of which there is located a valve 20 made of elastic material and having a slit 22 for the passage of urine therethrough.

The slit 22 is normally closed, as a result of the elasticity of the material of which the valve is made.

The portion of the duct 2, corresponding to the seat 21, is harder than the remaining part of the catheter, and this hardness is obtained by a special processing of the material in this zone while manufacturing the catheter.

As illustrated in FIG. 1, two winglets 25 are fixed to the outside end of the duct 2, symmetrically to the longitudinal axis of the catheter and of the valve 20.

The winglets 25 remain outside and rest against the top of the glans.

The winglets have a double function: first they prevent the catheter from sliding inside the urethra and second they allow the patient to operate the valve 20 from outside of the penis to evacuate urine.

The winglets 25 are harder than the rest of the catheter, as they are made of a different hardness material.

This hardness is preferably further increased by the presence of two reinforcement ribs 26 which extend along the winglet side which is turned toward the glans.

Pressing on the winglets causes, in conjunction with the reinforcement ribs, the deformation of the duct part correspondent to the seat 21, which in turn causes a pressing action on the sides of the valve and the opening, because of the elastic deformation of the latter, of the slit 22.

Therefore, the patient who normally retains urine with the valve 20 closed (position K, FIG. 4), makes the valve open (position H. FIG. 3) by applying a light pressure on the winglets 25.

The pressure will be applied during the whole period of time necessary to evacuate the urine completely.

In order to avoid the possible rotation of the valve 20 inside the relative seat 21, both the valve and seat may be made with a polygonal (FIG. 5) or an oval (FIG. 6) profile.

As an alternative, one or more blocking protrusions can be formed on the outside surface of the valve, as shown in FIG. 7, which are designed to engage with correspondent grooves made inside the seat.

In particular, the polygonal form of FIG. 5 is obtained by two planar opposing extensions of the surface of the valve 20.

A catheter manufactured in accordance with the present invention allows many people to obtain an improvement in their quality of life, avoiding many physical and psychological problems.

The result obtained by this invention was achieved using a particular production process that provides a different way of working a different part of the same article.

Also the material (silicone resin) was important to achieve the result, in conjunction with the production process.

I claim:

1. A valve operated catheter for urinary incontinence and retention comprising a flexible duct (2) for insertion into a patient's urethra and having a spiral shaped distal portion (12) for insertion inside a bladder, said distal portion provided with a plurality of holes (16) for the outflow of urine from the bladder to said duct, said catheter comprising:

a seat (21) provided at an end of the catheter that remains outside of a penis;

an elastically deformable valve (20) provided with a slit (22) that is normally closed, said valve (20) being housed inside said seat (21);

two winglets (25) fixed at the end of the duct (2), the winglets placed outside of the penis for resting against the top of the glans, such that the patient pressing on the winglets causes the deformation of the part of said duct (2) correspondent to said seat (21), and of said valve (20) until the slit (22) opens.

2. The catheter according to claim 1, wherein the part of said duct (2) correspondent to said seat (21) is harder than the remaining part of said duct (2).

3. The catheter according to claim 1, wherein said winglets (25) are harder than the remaining part of said catheter.

4. The catheter according to claim 1, further comprising a reinforcement rib formed along a side of each of said winglets that is turned towards the glans.

5. The catheter according to claim 1, wherein a profile of the valve (20) and of the seat (21) is polygonal.

6. The catheter according to claim 1, wherein a profile of the valve (20) and of the seat (21) is oval.

7. The catheter according to claim 1, further comprising at least one protrusion formed on an outer surface of said valve (20), said protrusion being designed to engage at least one correspondent groove provided inside said seat (21).

8. The catheter according to claim 1, wherein the distal portion (12) of said duct (2), positioned inside the bladder, has a shape of a spiral and is elastically deformable, said spiral having its axis perpendicular to the duct.

* * * * *